United States Patent [19]

Soll et al.

[11] Patent Number: 4,908,378
[45] Date of Patent: Mar. 13, 1990

[54] BENZOPYRAN DERIVATIVES AND ANTIHYPERTENSIVE USE THEREOF

[75] Inventors: Richard M. Soll, Lawrenceville, N.J.; Paul J. Dollings, Newtown, Pa.

[73] Assignee: American Home Products Corporation, New York, N.Y.

[21] Appl. No.: 336,966

[22] Filed: Apr. 12, 1989

[51] Int. Cl.$^4$ .................. C07D 405/04; A61K 31/40
[52] U.S. Cl. .................................. 514/414; 548/454; 548/472
[58] Field of Search ...................... 514/414; 548/454

[56] References Cited

U.S. PATENT DOCUMENTS 4,251,537 2/1981 Evans ................................. 424/267
4,616,021 10/1986 Ashwood et al. .................. 514/309

FOREIGN PATENT DOCUMENTS 158923 7/1982 European Pat. Off. .

Primary Examiner—David B. Springer
Attorney, Agent, or Firm—Walter Patton

[57] ABSTRACT

Disclosed herein are novel benzopyrans having pharmacological activity, to a process for preparing them, to pharmaceutical compositions containing them, and to their use in the treatment of hypertension.

8 Claims, No Drawings

BENZOPYRAN DERIVATIVES AND ANTIHYPERTENSIVE USE THEREOF

BACKGROUND OF THE INVENTION

The present invention relates to novel benzopyrans having pharmacological activity, to a process for preparing them, to pharmaceutical compositions containing them, and to their use in the treatment of hypertension.

Quagliato et al (U.S. Ser. No. 146,875, filed Jan. 22, 1988) discloses classes of chromans that are described as having blood pressure lowering activity. European Patent Publication 158,923 discloses classes of chromans that are described as having blood pressure lowering activity. In addition, U.S. Pat. Nos. 4,616,021 and 4,251,537 disclose classes of chromans that are described as having blood pressure lowering activity.

The present invention discloses compounds represented by formula (I)

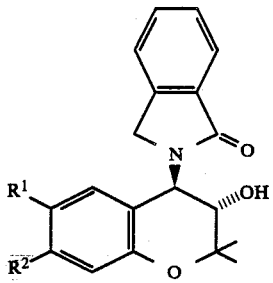

werein $R^1$ is trifluoromethylsulfonyl or trifluoromethylsulfinyl and $R^2$ is H; or $R^1$ is H or nitro and $R^2$ is $CF_3CONH$.

The compounds of formula (I), are asymmetric and, therefore, can exist in the form of optical isomers. The present invention extends to all such isomers individually and as mixtures, such as racemic modifications.

Preferably, a compound of formula (I) is in substantially pure form.

Examples of compounds of formula (I) include the compounds prepared in the Examples hereinafter.

The present invention also provides a process for the preparation of a compound of formula (I), which comprises the reaction of a compound of formula (II)

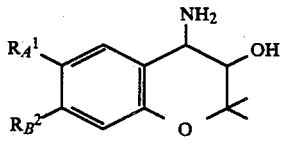

wherein $R^1$ and $R_B^2$ are $R^1$ and $R^2$ as defined respectively, hereinbefore or a group or atom convertible thereto with a compound of formula (III)

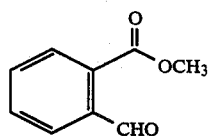

under reductive amination conditions.

It is particularly preferred that the reaction between the compounds of formula (II) and (III) is carried out under reducing conditions so as to facilitate the formation of the desired bonds, for example by warming in the presence of sodium cyanoborohydride.

Examples of conversions of a group or atom from $R_A^1$ into $R^1$ and $R_B^2$ into $R^2$ are generally known in the art of synthetic chemistry. For example, if it is desired to obtain a compound of formula (I) wherein $R^1$ is nitro and $R^2$ is $CF_3CONH$, it is possible to convert a compound of formula (I) wherein $R^1$ is H and $R^2$ is $NH_2$ or a protected $NH_2$ to the desired $R^1$ is $NO_2$ and $R^2$ is $CF_3CONH$ by nitration under standard conditions. Examples of protecting agents and their addition and removal are generally known in the art.

As mentioned previously, the compounds of formula (I) have been found to have blood-pressure lowering activity. They are therefore useful in the treatment of hypertension. Furthermore the compounds of formula (I) are active potassium channel activators which renders them useful in the treatment of cardiovascular diseases such as peripheral vascular disease, angina, congestive heart failure, and cerebral vascular disease, and in disorders involving excessive smooth muscle contraction of the gastro-intestinal tract (such as irritable bowel syndrome), respiratory system (such as asthma and reversible airways obstruction) and urinary tract (such as incontinence). Further, these compounds are useful in the treatment of baldness and hair loss.

The present invention accordingly provides a pharmaceutical composition which comprises a compound of this invention and a pharmaceutically acceptable carrier. In particular, the present invention provides an antihypertensive pharmaceutical composition which comprises an antihypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually 1 to 4 times a day.

The compositions of the invention may be formulated with conventional excipients, such as a filler, a disintegrating agent, a binder, a lubricant, a flavouring agent and the like. They are formulated in conventional manner, for example in a manner similar to that used for known antihypertensive agents, diuretics and -blocking agents.

The present invention further provides a compound of the invention for use as an active therapeutic substance. Compounds of formula (I) are of particular use in the treatment of hypertension.

The present invention further provides a method of treating hypertension in mammals including man, which comprises administering to the afflicted mammal an antihypertensive effective amount of a compound or a pharmaceutical composition of the invention.
Synthetic Process A relates to the preparation of the compounds of formula (I)
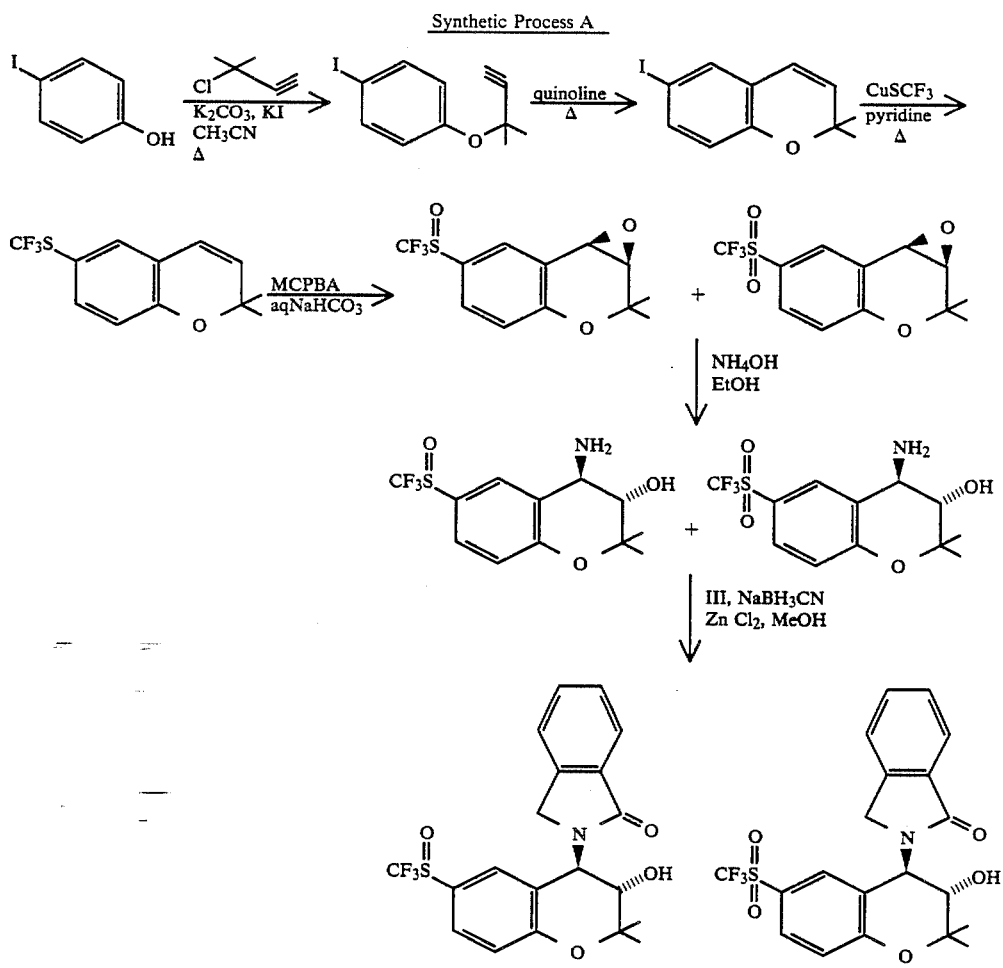
wherein $R^1$ is $SOCF_3$ or $SO_2CF_3$ and $R^2$ is H.
Synthetic Process B relates to the compound of Formula (I)
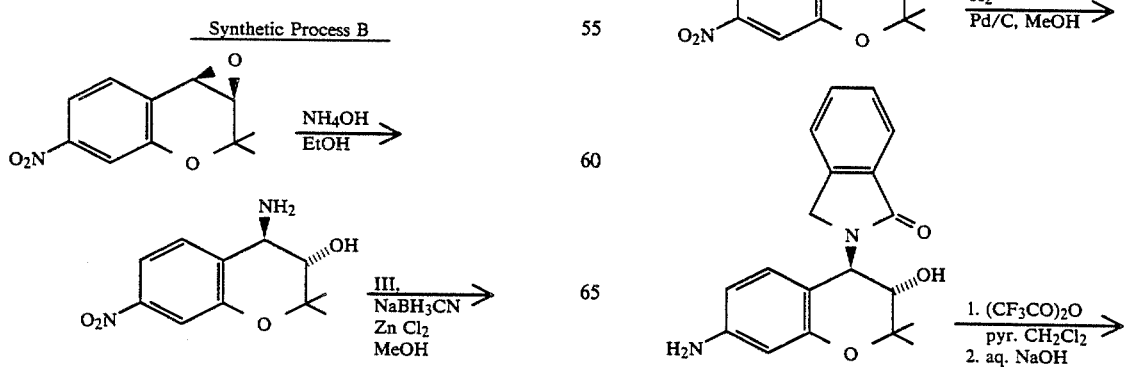

-continued
Synthetic Process B

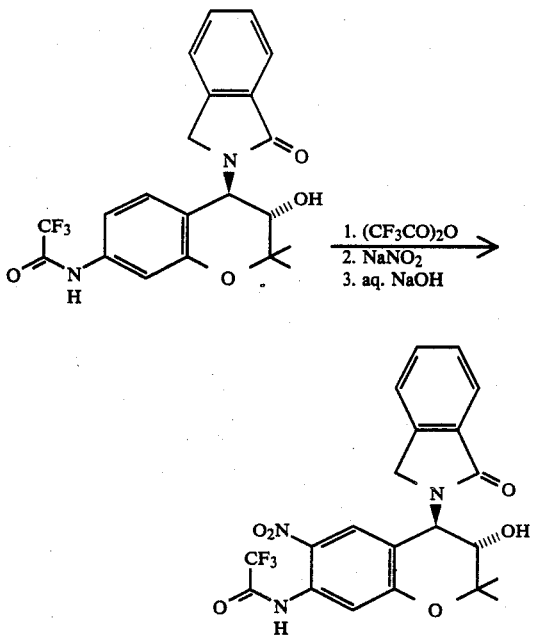

wherein R[1] is NO$_2$ and R[2] is CF$_3$CONH.

The following Examples further illustrate this invention.

EXAMPLE 1

Preparation of 1-[(1,1-Dimethyl-2-propynyl)oxy]-4-iodobenzene

To a solution of 4-iodophenol (5.01 g, 22.8 mmol) in CH$_3$CN (100 mL) containing K$_2$CO$_3$ (15.7 g, 0.114 mol) was added KI (4.91 g, 29.6 mmol) followed by 3-methyl-3-chlorobutyne (7.01 g, 68.3 mmol) at room temperature. The reaction was heated to 80° C. for 60 hours. The reaction was cooled to room temperature, quenched with 2.5N NaOH and extracted with ether. The combined organic extracts were washed with 2.5N NaOH (2X eq. vol.), dried over anhydrous K$_2$CO$_3$ and concentrated. The residue was taken up in a minimal amount of 10% ether/petroleum ether and filtered through a 2" silica gel pad, using 10% ether/petroleum ether elution. The filtrate was concentrated to give 6.04 g, (93%) of product.

$^1$H NMR (CDCl$_3$, 200 MHz): δ7.56 (d, 2H, Ar—H), 6.98 (d, 2H, Ar—H), 2.57 (s, 1H, C—H), 1.63 (s, 6H, C—CH$_3$).

EXAMPLE 2

Preparation of 2,2-Dimethyl-6-iodo-2H-benzopyran

A solution of 1-[(1,1-dimethyl-2-propynyl)oxy]-4-iodobenzene (5.97 g, 20.8 mmol) in quinoline (25 mL) was heated at 170° C. for 2 hours. The reaction was cooled to room temperature and diluted with ether. The reaction mixture was washed with 2N HCl (4X eq. vol.), with brine (2X eq. vol.), dried over anhydrous MgSO$_4$ and concentrated to give crude product. This material was combined with product from an identical reaction and purified by flash chromatography, using 100% petroleum ether elution to give 5.58 g, (79% for the two reactions), of product.

$^1$H NMR (CDCl$_3$, 200 MHz): δ7.35 (d, 1H, Ar—H), 7.25 (s, 1H, Ar—H), 6.54 (d, 1H, Ar—H), 6.23 (d, 1H, Ar—CH), 5.62 (d, 1H, CH), 1.41 (s, 6H, C—CH$_3$).

EXAMPLE 3

Preparation of 2,2-Dimethyl-6-(trifluoromethylmercapto)-2H-1-benzopyran

A mixture of Hg (SCF$_3$)$_2$ (1.73 g, 4.30 mmol) and copper dust (1.23 g, 19.3 mmol) was heated between 80°-100° C. for 2 hours then at 150° C. for 0.5 hours. The reaction was cooled to room temperature. To the reaction was added a deairated solution of 2,2-dimethyl-6-iodo-2H-benzopyran (1.02 g, 3.58 mmol) in pyridine (20 mL). The reaction was refluxed for 16 hours. The reaction was cooled to room temperature and diluted with ether (75 mL). The reaction mixture was washed with 2N HCl (4X eq. vol.), with brine (2X eq. vol.), dried over anhydrous MgSO$_4$ and concentrated. The crude product was purified by flash chromatography, using 100% petroleum ether, to give (0.645 g, (69%) of product.

$^1$H NMR (CDCl$_3$, 200 MHz): δ7.35 (dd, 1H, J=8.2 Hz), 7.25 (d, 1H, J=2 Hz), 6.78 (d, 1H, Ar—H), 6.30 (d, 1H, Ar—C—H), 5.66 (d, 1H), 1.45 (s, 6H).

EXAMPLE 4

Preparation of trans-2-[3,4-Dihydro-2,2-dimethyl-3-hydroxy-6-[(trifluoromethyl)sulfonyl]-2H-1-benzopyran-4-yl]-2,3-dihydro-1H-isoindol-1-one To a solution of 2,2-dimethyl-6-(trifluoromethylmercapto)-2H-1-benzopyran (5.6 g, 21.5 mmol) in CH$_2$Cl$_2$ (242 mL) was added saturated aqueous NaHCO$_3$ (242 mL) followed by 80% meta-chloroperoxybenzoic acid (18.6 g, 108 mmol) at room temperature. The reaction was stirred for 3 days. The reaction was treated with brine (300 mL) and extracted with CH$_2$Cl$_2$. The combined organic extracts were washed with saturated aqueous NaHCO$_3$ (3X eq. vol.), with brine (1X eq. vol.), dried over anhydrous K$_2$CO$_3$ and concentrated to give 9.0 g, crude product.

To a solution of 9.0 g, crude product in EtOH (270 mL), at room temperature, was added concentrated NH$_4$OH (270 mL). The reaction was stirred at room temperature for 16 hours. TLC showed product plus starting material. Additional EtOH (100 mL) and concentrated NH$_4$OH (270 mL) was added. The reaction was stirred for 1 day at room temperature. TLC showed no starting material. The reaction was quenched with brine (200 mL) and extracted with CH$_2$Cl$_2$. The combined organic extracts were washed with brine (3X eq. vol.), dried over anhydrous K$_2$CO$_3$ and concentrated to give 7.1 g, crude product.

To a solution of 7.1 g of crude product in methanol (70 mL) containing 2-carbomethoxybenzaldehyde (4.23 g, 25.8 mmol) was added 86 mL (43.0 mmol) of 0.5M zinc chloride-modified sodium cyanoborohydride in methanol, as prepared by the method of Kim et al. *J. Org. Chem.*, 50 (11), 1927 (1985). After refluxing for 16 hours, the reaction was cooled to room temperature, quenched with H$_2$O (100 mL) and extracted with 20% THF/CH$_2$Cl$_2$. The combined organic extracts were washed with brine (3 portions) and concentrated. The crude product was purified by flash chromatography, using 15% CH$_3$CN/CH$_2$Cl$_2$ elution to give 1.44 g, of the desired sulphone as a colorless solid m.p. 275°–277° C.

$^1$H NMR (acetone, 400 MHz): δ7.89 (d of d, 1H, Ar—H), 7.81 (d, 1H, Ar—H), 7.65–7.54 (m, 4H, Ar—H), 7.23 (d, 1H, Ar—H), 5.54 (br d, 1H, Ar—CH), 4.62 (d, 1H, Ar—CH), 4.30–4.20 (m, 2H, Ar—CH and CH—O), 1.61 (s, 3H, —CH$_3$), 1.43 (s, 3H, —CH$_3$)

IR: 3600–3200 (O—H), 1670 (C=O), 1350 and 1120 cm$^{-1}$.

MS: 442 (M+).

Anal. Calcd. for $C_{20}H_{18}F_3NO_5S$: C, 54.47; H, 4.11; N, 3.18%. Found: C, 54.74; H, 4.45; N, 2.69%.

EXAMPLE 5

Preparation of trans-2-[3,4-Dihydro-2,2-dimethyl-3-hydroxy-6-[(trifluoromethyl)sulfinyl]-2H-1-benzopyran-4-yl]-2,3-dihydro-1H-isoindol-1-one Using the method of Example 4, continued flash chromatography elution with 30% CH$_3$CN/CH$_2$Cl$_2$ provided 0.78 g of the title compound as a colorless solid, m.p. 253°–258° C.

$^1$H NMR (acetone, 400 MHz): δ7.80 (d of d, 1H, Ar—H), 7.72 (d, 1H, Ar—H), 7.61–7.53 (m, 3H, Ar—H), 7.43 (d, 1H, Ar—H), 7.16 (d of d, 1H, Ar—H), 5.56 (d, 1H, Ar—CH), 4.54 (d, 1H, Ar—CH), 4.20–4.08 (m, 2H, Ar—CH and CH—O), 1.58 (s, 3H, —CH$_3$), 1.39 (s, 3H, —CH$_3$)

IR: 3600–3200 (O—H), 1670 (C=O) cm$^{-1}$.

MS: 426 (M+).

Anal. Calcd. for $C_{20}H_{18}F_3NO_4S$: C, 56.52; H, 4.27; N, 3.30%. Found: C, 56.59; H, 4.60; N, 3.28%.

EXAMPLE 6

Preparation of trans-3,4-Dihydro-2,2-dimethyl-3-hydroxy-7-nitro-2H-1-benzopyran-4-amine A mixture of 1.09 g (5.31 mmol) of 2,2-dimethyl-7-nitro-2H-1-benzopyran, prepared as described by Evans et al *J. Med. Chem.* 26 (11), 1582 (1983), 2.3 g (10.7 mmol) of meta-chloroperoxybenzoic acid (80% strength) in 30 mL of methylene chloride and 30 mL of 0.5M aqueous sodium bicarbonate as stirred at ambient temperature for two days. The reaction mixture was diluted further with aqueous sodium bicarbonate, quenched with 20% bisulfite solution and extracted into ether. The organic phase was dried (K$_2$CO$_3$) and concentrated.

A mixture of the crude product in 10 mL of concentrated NH$_4$OH and 10 mL EtOH was stirred at room temperature overnight. The reaction mixture was diluted with water and was extracted into ether. The ethereal phase was extracted into 1N HCl. The aqueous extract was basified with 2.5N NaOH, extracted into ether, dried (K$_2$CO$_3$), and concentrated to give 373 mg of product as a yellow powder, m.p. 159°–163° C.

$^1$H NMR (CDCl$_3$; 200 MHz): δ7.78 (dd, 1H), 7.64 (d, 1H), 7.56 (d, 1H), 3.72 (d, 1H), 3.39 (d, 1H), 1.75 (bs, 3H), 1.54 (s, 3H), 1.24 (s, 3H).

IR (KBr): 3425, 3290, 3100 and 1530 cm$^{-1}$.

MS (m/e): 239 (M+H+), 167.

Anal. Calcd. for $C_{11}H_{14}N_2O_4 \cdot \frac{1}{2}H_2O$: C, 54.08; H, 6.06; N, 11.47%. Found: C, 54.04; H, 5.94; N, 11.06%.

EXAMPLE 7

Preparation of trans-2-(3,4-Dihydro-2,2-dimethyl-3-hydroxy-7-nitro-2H-1-benzopyran-4-yl)-2,3-dihydro-1H-isoindol-1-one To 351 mg (1.48 mmol) of trans-3,4-dihydro-2,2-dimethyl-3-hydroxy-7-nitro-2H-1-benzopyran-4-amine in methanol (3 mL) containing 290 mg (1.77 mmol) of 2-carbomethoxybenzaldehyde was added 1.5 mL (0.75 mmol) of 0.5M zinc chloride-modified sodium cyanoborohydride in methanol, prepared according to the method of Kim et al. *J. Org. Chem.* 50 (11), 1927 (1985). After stirring at 50° C. for two days, the reaction mixture was quenched with saturated NaHCO$_3$ solution, extracted into CH$_2$Cl$_2$, dried (K$_2$CO$_3$) and concentrated. The residue was dissolved in a minimal amount of THF and silica gel was added. The solvent was removed in vacuo and the silica gel was applied onto the head of a flash column. Eluting with 20%→50% ether/CH$_2$Cl$_2$ gave 390 mg of the title compound as a pale yellow powder, m.p. 249°–250° C.

$^1$H NMR (CDCl$_3$; 400 MHz) δ7.75 (d, 1H), 7.73 (d, 1H), 7.67 (d, 1H), 7.52 (t, 1H), 7.41 (s, 1H), 7.39 (d, 1H), 7.04 (d, 1H), 5.62 (d, 1H), 4.41 (d, 1H), 4.11 (d, 1H), 3.99 (dd, 1H), 3.65 (d, 1H), 1.60 (s, 3H), 1.39 (s, 3H).

IR (KBr): 3490, 1675 and 1520 cm$^{-1}$.

MS (m/e): 355 (M+H+), 337, 321.

Anal. Calcd. for $C_{19}H_{18}N_2O_5 \cdot \frac{1}{4}H_2O$: C, 63.32, H, 5.23; N, 7.78%, Found: C, 63.05, H, 5.42, N, 7.63%.

EXAMPLE 8

Preparation of trans-2-(3,4-Dihydro-2,2-dimethyl-3-hydroxy-7-amino-2H-1-benzopyran-4-yl)-2,3-dihydro-1H-isoindol-1-one A mixture of 1.01 g (2.85 mmol) of trans-2-(3,4-dihydro-2,2-dimethyl-3-hydroxy-7-nitro-2H-1-benzopyran-4-yl)-2,3-dihydro-1H-isoindol-1-one and 250 mg of 10% Pd/C in methanol (30 mL) was hydrogenated at atmospheric pressure for 4 hours. Filtration through Solka Floc ® using a methanol rinse and concentration gave crude title compound which was used without further purification.

$^1$H NMR (200 MHz; CDCl$_3$): δ7.80 (d, 1H), 7.35–7.55 (m, 3 Hz9, 6.64 (d, 1H), 6.20 (d, 1H), 6.18 (s, 1H), 5.50 (d, 1H), 4.30 (d, 1H), 4.17 (d, 1H), 3.86 (d, 1H), 3.65 (2H, NH$_2$), 3.34 (bs, 1H, OH), 1.52 (s, 3H), 1.33 (s, 3H).

EXAMPLE 9

Preparation of trans-N-[3,4-Dihydro-3-hydroxy-2,2-dimethyl-4-(1,3-dihydro-2-oxo-2H-isoindol-2-yl)-2H-1-benzopyran-7-yl]-2,2,2-trifluoroacetamide At 0° C. to 978.5 mg of trans-2-(3,4-dihydro-2,2-dimethyl-3-hydroxy-7-amino-2H-1-benzopyran-4-yl)-2,3-dihydro-1H-isoindol-1-one in CH$_2$Cl$_2$ (30 mL) containing 1.47 mL (18.2 mmol) of pyridine was added slowly 2.0 mL (14.2 mmol) of trifluoroacetic anhydride. After stirring at room temperature for 1 hour, a solution resulted. The reaction mixture was quenched at 0° C. with 20 mL of 1N NaOH and was stirred at 0° C. for 15 minutes. Acidification with 1N HCl extractive workup with CH$_2$Cl$_2$, drying (MgSO$_4$) and concentration gave crude material which clearly showed N- and O-trifluoroacetylated material. The material was dissolved in acetonitrile (20 mL) and was treated with 20 mL of 1N NaOH. After 15 minutes, the reaction mixture was acidified with 10% citric acid, extracted with CH$_2$Cl$_2$, dried (MgSO$_4$) and concentrated to give 872 mg (69%) of the crude title compound.

$^1$H NMR (200 MHz; d$_6$ acetone): δ7.81 (d, 1H), 7.53-7.78 (m, 3H), 7.40 (d, 1H), 7.13 (dd, 1H), 6.87 (d, 1H), 5.49 (d, 1H), 4.50 (d, 1H), 4.12 (d, 1H), 4.08 (d, 1H), 1.54 (s, 3H), 1.35 (s, 3H).

IR (KBr): 3540, 1715 and 1675 cm$^{-1}$.

MS (m/e): 421, (M+1), 402, 387.

EXAMPLE 10

Preparation of trans-N-[3,4-Dihydro-3-hydroxy-2,2-dimethyl-6-nitro-4-(1,3-dihydro-2-oxo-2H-isoindol-2-yl)-2H-1-benzopyran-7-yl]-2,2,2-trifluoroacetamide At 0° C. to 872 mg (2.08 mmol) of trans-N-[3,4-dihydro-3-hydroxy-2,2-dimethyl-4-(1,3-dihydro-2-oxo-2H-isoindol-2-yl)-2H-1-benzopyran-7-yl]-2,2,2-trifluoroacetamide in 50 mL of acetonitrile was added 2.4 mL (17 mmol) of trifluoroacetic anhydride. After 1 hour at 0° C., 204 mg (2.55 mmol) of ammonium nitrate was added. After 10 minutes, the reaction mixture was basified at 0° C. with 2N NaOH. After 15 minutes, the reaction mixture was quenched with 10% citric acid, extracted into CH$_2$Cl$_2$, dried (MgSO$_4$) and flash chromatographed (1:2 acetone/petroleum ether) to give 448 mg (38%) of pure title compound as a yellow powder, m.p. 279° C.

$^1$H NMR (400 MHz; d$_6$-DMSO): δ11.5 (s, 1H), 7.79 (d, 1H), 7.64 (t, 1H), 7.5-7.6 (m, 3H), 7.13 (s, 1H), 5.91 (d, 1H), 1.51 (s, 3H), 1.29 (s, 3H)

IR (KBr): 3480, 3260, 1745 and 1675 cm$^{-1}$,

MS (m/e): 466 (M+H$^+$), 447, 432.

Anal. Calcd. for C$_{21}$H$_{18}$F$_3$N$_3$O$_6$: C, 54.19; H, 3.91; N, 9.02%, Found: C, 54.11; H, 4.55; N, 8.39%.

Pharmacological Data

Male Okamoto-Aoki spontaneously hypertensive rats (SHR) ranging in weight from 250-400 g were anesthetized with halothane. Their left femoral arteries and veins were cannulated with polyethylene tubing of the appropriate size (i.d. 0.023", o.d. 0.038"). Each animal was placed in a Bollman cage, and the tail, along with two cannulas, was extended through a hole in one end of the cage. The tail was taped securely to a firm rubber board to prevent the rate from turning in its cage to dislodge the cannulas. The femoral arterial cannula was connected to a Statham pressure transducer which in turn was attached to a polygraph for recording arterial pressure and pulse rate. The pulse rate was considered to be the heart rate.

After the blood pressure had stabilized (usually 2 hours after cessation of the anesthesia), standard agonists were injected by the i.v. route. The doses administered were: isoproterenol 0.5 μg/kg, adrenaline 2.0 μg/kg, tyramine 200 μg/kg and angiotensin-I 0.25 μg/kg. The agonists were given in random order except that tyramine was never preceded by isoproterenol as the response to tyramine seemed to be blunted after a prior injection of isoproterenol. Enough time was allowed for the BP to return to preinjection levels before the test compound was administered by gastric lavage. The time of drug administration was designated as time zero. Heart rate and blood pressure were recorded at 5, 10, 15, 30, 45 and 60 minutes and hourly thereafter for a period of 4 hours after drug administration. At 1 and 2 hours post-drug the agonists were again injected at the same concentration and in the same order as during the control period.

For each compound the maximum mean fall in blood pressure was compared to pretreatment control values and expressed as a percentage fall in blood pressure.

Blood Pressure Lowering by Compounds of Formula (I)

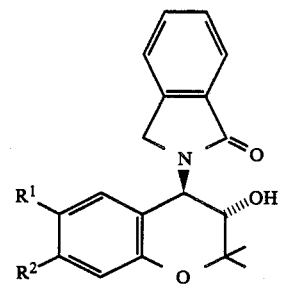

(I)

| Compound | mg/kg p.o. | n | Pre-treat. MABP mm Hg | Max Δ BP mm Hg | % | Pre-treat. HR beats/min. | Max Δ HR beats | % |
|---|---|---|---|---|---|---|---|---|
| R$^1$ = NO$_2$ | 10 | 2 | 186 | −127 (15 min) | −68 | 365 | +106 (15 min) | +29 |
| R$^2$ = NHCOCF$_3$ | 0.1 | 4 | 177 | −69 (5 hrs) | −39 | 357 | +78 (4 hrs) | +22 |
|  | 0.08 | 8 | 180 ± 3 | −59 (4 hrs) | −33 | 355 ±12 | +94 (4 hrs) | +27 |
|  |  |  |  | −13 (12 hrs) | −7 |  |  |  |
|  | 0.03 | 4 | 179 | −34 (5 hrs) | −19 | 370 | +47 (4 hrs) | +13 |
|  | 0.01 | 4 | 183 | −17 (4 hrs) | −9 | 386 | −38 (4 hrs) | −10 |
| R$^1$ = SOCF$_3$ | 10 | 2 | 185 | −111 (30 min) | −60 | 365 | +120 (30 min) | +33 |
| R$^2$ = H | 0.1 | 3 | 185 | −40 (4 hrs) | −22 | 386 | +24 (4 hrs) | +6 |
| R$^1$ = SO$_2$CF$_3$ | 10 | 2 | 175 | −79 (45 min) | −45 | 370 | +111 (45 min) | +30 |
| R$^2$ = H | 0.1 | 4 | 189 | −15 (4 hrs) | −8 | 364 | +29 (4 hrs) | +8 |

Compounds of formula (I) may be administered alone or with a diuretic, such as hydrochlorothiazide, or a β-blocker, such as propranolol or cetamolol in a suitable unit dose form.

We claim:

1. A compound of formula (I)

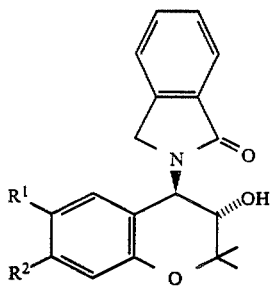

(I)

wherein $R^1$ is trifluoromethylsulfonyl or trifluoromethylsulfinyl and $R^2$ is H; or $R^1$ is H or nitro and $R^2$ is $CF_3CONH$.

2. The compound according to claim 1 which is trans-2-[3,4-dihydro-2,2-dimethyl-3-hydroxy-6-[(trifluoromethyl)sulfonyl]-2H-1-benzopyran-4-yl]-2,3-dihydro-1H-isoindol-1-one.

3. The compound according to claim 1 which is trans-2-[b  3,4-dihydro-2,2-dimethyl-3-hydroxy-6-[(trifluoromethyl)sulfinyl]-2H-1-benzopyran-4-yl]-2,3-dihydro-1H-isoindol-1-one.

4. The compound according to claim 1 wich is trans-N-[3,4-dihydro-3-hydroxy-2,2-dimethyl-6-nitro-4-(1,3-dihydro-2-oxo-2H-isoindol-2-yl)-2H-1-benzopyran-7-yl]-2,2,2-trifluoroacetamide.

5. The compound according to claim 1 which is trans-N-[3,4-dihydro-3-hydroxy-2,2-dimethyl-4-(1,3-dihydro-2-oxo-2H-isoindol-2-yl)-2H-1-benzopyran-7-yl]-2,2,2-trifluoroacetamide.

6. The compound 2,2-dimethyl-6-(trifluoromethylmercapto)-2H-benzopyran.

7. A pharmaceutical composition comprising a compound according to claim 1 and a pharmaceutically acceptable carrier for use in the treatment of hypertension.

8. A method of treatment of hypertension in mammals which comprises administering to the mammal in need thereof an effective antihypertensive amount of a compound of formula (I).

* * * * *